(12) United States Patent
Lin (10) Patent No.: US 10,092,925 B2
(45) Date of Patent: Oct. 9, 2018

(54) METHOD FOR CONTINUOUSLY MANUFACTURING MOISTURE FILM

(71) Applicant: Biosol Tech Corporation Limited, New Taipei (TW)

(72) Inventor: Yu-Yueh Lin, Taipei (TW)

(73) Assignee: BIOSOL TECH CORPORATION LIMITED, New Taipei (TW)

( * ) Notice: Subject to any disclaimer, the term of this patent is extended or adjusted under 35 U.S.C. 154(b) by 301 days.

(21) Appl. No.: 15/045,776

(22) Filed: Feb. 17, 2016

(65) Prior Publication Data

US 2016/0158796 A1 Jun. 9, 2016

Related U.S. Application Data

(62) Division of application No. 14/304,706, filed on Jun. 13, 2014, now Pat. No. 9,555,440.

(51) Int. Cl.
| | |
|---|---|
| *B05D 1/02* | (2006.01) |
| *B05B 13/02* | (2006.01) |
| *A61F 13/15* | (2006.01) |
| *B01J 20/28* | (2006.01) |
| *D06B 1/00* | (2006.01) |

(Continued)

(52) U.S. Cl.
CPC ............. *B05D 1/02* (2013.01); *A61F 13/15* (2013.01); *A61K 8/0208* (2013.01); *A61K 8/733* (2013.01); *A61Q 19/00* (2013.01); *B01J 20/28038* (2013.01); *B05B 13/0221* (2013.01); *B05D 1/18* (2013.01); *B32B 5/02* (2013.01); *B32B 5/22* (2013.01); *B32B 5/26* (2013.01); *D06B 1/00* (2013.01); *D06B 1/02* (2013.01); *A61K 2800/805* (2013.01); *B05B 13/0463* (2013.01); *B32B 2255/02* (2013.01); *B32B 2255/28* (2013.01); *B32B 2260/021* (2013.01); *B32B 2307/726* (2013.01)

(58) Field of Classification Search
CPC ... B05D 1/36; B05D 1/38; B05D 7/56; B05D 7/572; B05D 7/58
See application file for complete search history.

(56) References Cited

U.S. PATENT DOCUMENTS

| | | |
|---|---|---|
| 5,144,016 A | 9/1992 | Skjak-Braek et al. |
| 5,230,853 A | 7/1993 | Colegrove et al. |
| (Continued) | | |

FOREIGN PATENT DOCUMENTS

| | | |
|---|---|---|
| EP | 2 111 926 A1 | 10/2009 |
| JP | 2010-189386 A | 9/2010 |
| (Continued) | | |

*Primary Examiner* — Scott W Dodds
(74) *Attorney, Agent, or Firm* — Muncy, Geissler, Olds & Lowe, P.C.

(57) ABSTRACT

An apparatus and a method for continuously manufacturing moisture films are revealed. At least one loading surface formed by a belt conveyor is used to support and move a lower fabric layer synchronously. During the movement, a top surface of the lower fabric layer is coated with a first fixing solution layer, a gel layer and a second fixing solution layer so as to form a film gradually. Moreover, an upper fabric layer is provided to be attached over the gel layer correspondingly. Then the second fixing solution layer is coated over the upper fabric layer. Thereby a continuous manufacturing of moisture films with or without carriers is completed.

3 Claims, 9 Drawing Sheets

(51) Int. Cl.
*B32B 5/02* (2006.01)
*B32B 5/22* (2006.01)
*B32B 5/26* (2006.01)
*A61K 8/73* (2006.01)
*A61Q 19/00* (2006.01)
*A61K 8/02* (2006.01)
*B05D 1/18* (2006.01)
*D06B 1/02* (2006.01)
*B05B 13/04* (2006.01)

(56) References Cited

U.S. PATENT DOCUMENTS

| | | | |
|---|---|---|---|
| 5,622,666 A | 4/1997 | Struszczyk et al. | |
| 5,660,857 A | 8/1997 | Haynes et al. | |
| 5,675,957 A | 10/1997 | Kim | |
| 6,080,420 A | 6/2000 | Qin et al. | |
| 6,201,164 B1 | 3/2001 | Wulff et al. | |
| 6,203,845 B1 | 3/2001 | Qin et al. | |
| 6,258,995 B1 | 7/2001 | Gilding et al. | |
| 6,326,524 B1 | 12/2001 | Fattman et al. | |
| 6,372,248 B1 | 4/2002 | Qin et al. | |
| 2005/0255249 A1* | 11/2005 | Schlatterbeck | B05B 12/04 427/372.2 |
| 2005/0287193 A1 | 12/2005 | Lee | |
| 2010/0227164 A1 | 9/2010 | Hihnala et al. | |

FOREIGN PATENT DOCUMENTS

| | | |
|---|---|---|
| WO | WO 96/10106 | 4/1996 |
| WO | WO 97/03710 | 2/1997 |
| WO | WO 97/39781 | 10/1997 |
| WO | WO 98/02196 | 1/1998 |
| WO | WO 99/20378 | 4/1999 |
| WO | WO 03/092754 A1 | 11/2003 |
| WO | WO 2008/072817 A1 | 10/2009 |

* cited by examiner

METHOD FOR CONTINUOUSLY
MANUFACTURING MOISTURE FILM

CROSS-REFERENCE TO RELATED
APPLICATIONS

This application is a Divisional of co-pending application Ser. No. 14/304,706, filed on Jun. 13, 2014, for which priority is claimed under 35 U.S.C. § 120, the entire contents of all of which are hereby incorporated by reference.

BACKGROUND OF THE INVENTION

The present invention relates to an apparatus and a method for continuously manufacturing moisture films, especially to an apparatus and a method for continuously manufacturing moisture films that include at least one loading surface formed by at least one belt conveyor and used for supporting a lower fabric layer to produce films continuously. The lower fabric layer is moved synchronously with the loading surface and is coated with a first fixing solution layer, a gel layer, and a second fixing solution layer in turn. Thus a film is gradually formed over the lower fabric layer and a continuous manufacturing of moisture films with or without carriers is completed.

The film-forming materials of the present invention include, but not limited to alginic acid and salt compound of alginic acid (alginate). The alginic acid (so-called gel in the present invention) is a natural polymer, easy to react with salt compounds (such as the first and the second fixing solutions in the present invention, but not limited to) to form alginate film (the film in the present invention). For example, water-soluble sodium alginate (gel) reacts with divalent calcium ions in salt compound solution (fixing solution). Thus crosslinking and curing reactions occur to form insoluble calcium alginate film. During the manufacturing process, the film is produced into a long, continuous/ or non-continuous strip with a certain width (but not limited to) and is treated by following processing including cutting masks with required shapes by cutting dies. The masks are applied to cosmetic moisture masks. The so-called film in the present invention is used as facial mask so that the film can also be called as masks. In the present invention, a film with larger area is produced first and then the film is cut into a plurality of masks with certain shaped by cutting dies.

Refer to U.S. Pat. No. 6,080,420, U.S. Pat. No. 6,258,995, U.S. Pat. No. 6,203,845, U.S. Pat. No. 6,201,164, U.S. Pat. No. 6,372,248, U.S. Pat. No. 6,326,524, U.S. Pat. No. 5,144,016, U.S. Pat. No. 5,230,853, U.S. Pat. No. 5,622,666, U.S. Pat. No. 5,660,857, U.S. Pat. No. 5,675,957, U.S. Pat. No. 5,144,016, US2005/0287193, US2010/0227164, PCT/ GB 9502284 (WO96/10106), PCT/GB 9601719 (WO97/ 03710), PCT/GB 9701098 (WO97/39781), PCT/DK 9700292 (WO98/02196), WO2008/072817, WO03092754, EP2111926A1 (WO2008/0090892, PCT/JP2008/050822); JP2010-189386, WO99/20378A1, these are all prior arts related to moisture films (masks). However, most of these prior arts are focused on film composition or weight percent of each component in the film.

Yet there are no technical solutions for problems such as how the moisture films are mass-produced or how the cost is reduced.

Moreover, the moisture film (mask) is divided into two types while in use-without carriers or with carriers. The moisture film without carriers includes only a film with a certain thickness such as alginate mask while the moisture film with carriers consists of a film with a certain thickness and a thin layer of the carrier such as non-woven fabric connected to each other. Generally, the thin layer of the carrier is contained in and integrated with the film so that the film and the carrier are unable or difficult to be separated.

As to the package pattern of the moisture film (mask), the moisture film with or without carriers is folded or directly stored in, but not limited to, a sealed bag with specific solution (such as saline solution for keeping the film moisture or essence/serum for face care). While in use, consumers open the sealed bag and take the moisture film out. The moisture film with or without carriers is a soft and thin membrane. For ease of movement during manufacturing/ packaging and convenience in use, a protection film is attached to at least one surface of the moisture film with or without carriers at the manufacturing end. For example, a piece of pearl paper is attached to one surface of the moisture film for supporting during packaging or storage while the other surface of the moisture film is attached with a non-woven fabric layer that allows the solution in the sealed bag to pass and infiltrate into the film. In the present invention, the protection film attached is different from the thin layer of carrier in the moisture film with carriers.

Furthermore, the apparatus or the method for continuously manufacturing moisture films available now has following disadvantage:

First, the moisture film is a soft and thin gel membrane. Thus manufacturing and cutting of the membrane are not so easy. For ease of manufacturing or cutting into shapes required, the inventor proposes an idea that a flat loading surface or a lower fabric layer is used for transporting the moisture film. And the whole film-forming process has been completed during the movement.

Refer to EP2111926A1 (PCT/JP2008/050822, WO2008/ 0090892), the moisture films with or without carriers are unable to be produced continuously and quickly at the manufacturing end. The manufacturing of the moisture films includes at least coating process of gel (alginic acid) and related device (or working station), coating process of fixing solutions (such as salt compound) and related device (or working station), a device (or working station) in which crosslinking reaction between the gel and the fixing solutions, and/or a device (or working station) for stopping the crosslinking reaction between the fixing solutions and the gel, curing and forming soft moisture films. However, the arrangement of these devices is not efficient. For example, an impregnation coater and a gravure coater are two main workings stations and are separated from each other. Then a continuous supporting material is passed through the above two working stations by turning or traction effect of a plurality of idler wheels or rotating wheels for coating salt compound (fixing solutions) and alginic acid (gel) on the surface of the continuous supporting material. There is no continuous conveyor used to load the supporting material in the whole manufacturing apparatus. Thus each film-forming material such as alginic acid (gel) or salt compound (fixing solutions) is unable to be coated continuously and quickly to form the films. Moreover, several conveys (such as idler wheels or rotating wheels) are required to connect the separated working stations (as shown in FIGS. 2-4 EP2111926A1) at the manufacturing end so that manufacturing of the moisture films can be performed and completed. Thus the whole apparatus and the manufacturing process are more complications and a larger space is occupies. This leads to increasing cost in the apparatus and the manufacturing. And the manufacturing is not a continuous and rapid process.

The third one is that the moisture films are divided into two types-without carriers and with carriers. In prior arts, the same apparatus at the manufacturing end is unable to be used for manufacturing both types of moisture films by simple replacement or modification of devices or working stations in the apparatus. Generally, a new apparatus is designed and used to produce new type of moisture films. This causes a waste, increasing cost and ore space for the new apparatus. The competitiveness is greatly influenced.

There is room for improvement and a need to provide a new design of an apparatus and a method for manufacturing moisture films that overcome above shortcomings.

SUMMARY OF THE INVENTION

Therefore it is a primary object of the present invention to provide an apparatus for continuously manufacturing moisture films that includes at least one circulating loading surface that is a flat surface facing upward and formed by a belt conveyor. The belt conveyor is moved from an input end (front end) to an output end (rear end) along a conveying direction. A lower fabric layer with water absorbency is arranged at the loading surface and moved backward synchronously with the loading surface to receive various film-forming materials such as fixing solutions and gel for film formation. The following devices are arranged over the loading surface in turn from the input end to the output end. A first fixing solution coating device is used for coating a first fixing solution layer over the lower fabric layer. Then a gel coating device is used to coat a gel layer over the first fixing solution layer for performing crosslinking and curing reactions in an upward direction. A second fixing solution coating device is for coating a second fixing solution layer over the gel layer and carrying out crosslinking and curing reactions in a downward direction. Thereby a film with a certain thickness is gradually formed on a top surface of the lower fabric layer during the synchronous movement of the lower fabric layer with the loading surface and a continuous manufacturing of moisture films without carriers is completed. Therefore both mass production and cost reduction are achieved.

It is another object of the present invention to provide an apparatus for continuously manufacturing moisture films that further includes an upper fabric input device is disposed between the gel coating device and the second fixing solution coating device. An upper fabric layer provided by the upper fabric input device is attached over the gel layer correspondingly. Then the second fixing solution layer is coated over the upper fabric layer so that the upper fabric layer is clipped between the second fixing solution layer and the gel layer after the crosslinking and curing reaction. Thereby a film with a certain thickness and containing the upper fabric layer is gradually formed on a top surface of the lower fabric layer that is moved synchronously with the loading surface. And the original continuous manufacturing of moisture films without carriers is converted to a continuous manufacturing process of moisture films with carriers. Not only mass production and cost reduction are achieved, the types of the moisture film and its convenience of use are also improved.

It is a further object of the present invention to provide an apparatus for continuously manufacturing moisture films that includes a crosslinking control area disposed after the second fixing solution coating device. The moisture film passed through the second fixing solution coating device is washed at the crosslinking control area so that the crosslinking reaction between the fixing solution and the gel in the film is stopped. Thus the flexibility of the film formed can be controlled during manufacturing.

It is a further object of the present invention to provide a method for continuously manufacturing moisture films including following steps. Step 1: provide at least one circulating loading surface used as a working platform for film-forming. The loading surface is a flat surface facing upward and moved circularly along a conveying direction from an input end to an output end. Step 2: provide a lower fabric layer with water absorbency that is moved synchronously with the loading surface for receiving various film-forming materials in turn in and performing film-forming operation. Step 3: provide a first fixing solution coating device that coats a first fixing solution layer over the lower fabric layer. Step 4: provide a gel coating device for coating a gel layer over the first fixing solution layer and having crosslinking and curing reactions in an upward direction therebetween. Step 5: provide a second fixing solution coating device used to coat a second fixing solution layer over the gel layer for carrying out crosslinking and curing reactions mostly in a downward direction. Thus a film with a certain thickness is gradually formed on a top surface of the lower fabric layer moved synchronously with the loading surface. Thereby a continuous manufacturing of the moisture film without carriers is completed.

It is a further object of the present invention to provide a method for continuously manufacturing moisture films that includes following steps. Step 1: provide at least one circulating loading surface used as a working platform for film-forming. The loading surface is a flat surface facing upward and moved circularly along a conveying direction from an input end to an output end. Step 2: provide a lower fabric layer with water absorbency that is moved synchronously with the loading surface for receiving various film-forming materials in turn in and performing film-forming operation. Step 3: provide a first fixing solution coating device used for coating a first fixing solution layer over the lower fabric layer. Step 4: provide a gel coating device for coating a gel layer over the first fixing solution layer and having crosslinking and curing reactions in an upward direction therebetween. Step 5: provide an upper fabric layer attached over the gel layer correspondingly. Step 6: provide a second fixing solution coating device used to coat a second fixing solution layer over the upper fabric layer for carrying out crosslinking and curing reactions mostly in a downward direction. The upper fabric layer is clipped between the second fixing solution layer and the gel layer. Thereby a film with a certain thickness and containing the upper fabric layer is gradually formed on a top surface of the lower fabric layer that is moved synchronously with the loading surface and a continuous manufacturing of the moisture film with carriers is completed.

The lower fabric layer is moveably arranged at the loading surface of the belt conveyor. A roll of the lower fabric layer is disposed in front of the belt conveyor so that the lower fabric layer is passed through the input end and continuously input over the loading surface. Thus the continuous lower fabric layer is moved synchronously with the loading surface to receive various film-forming materials for film formation on the surface thereof. Then the continuous lower fabric layer still supports and moves the film formed to following working stations for follow-up operations.

The lower fabric layer is fixed on the loading surface of the belt conveyor. The lower fabric layer is directly disposed over and moved synchronously with the loading surface of the belt conveyor for receiving various film-forming materials for film formation on the surface thereof. Thus a long strip of the film is formed on the surface of the lower fabric layer over the loading surface of the belt conveyor. After the film-forming process being completed, the lower fabric layer is circularly rotated with the loading surface of the belt conveyor. As to the long strip of the film already formed, it is separated from the lower fabric layer over the loading surface and moved backward to one of follow-up working stations.

A follow-up operation area is disposed after the output end of the circulating loading surface of the belt conveyor. By at least one circulating operation surface that is facing upward, moved along a conveying direction and formed by a belt conveyor, the moisture film without or with carriers already produced is moved backward and entered the follow-up operation area for follow-up processing.

DETAILED DESCRIPTION OF THE PREFERRED EMBODIMENTS

The embodiments of the present invention are shown by side view schematic drawings from FIG. 1 to FIG. 9. The moving direction/conveying direction of an apparatus for continuously manufacturing moisture film of the present invention is from the left side toward the right side from FIG. 1 to FIG. 9. The left side in the figures is defined as the front side while the right side in the figures is defined as the rear side. The direction perpendicular to the surface of the paper with the figures is defined as the width direction. For convenience of description, a lower fabric layer 20, a first fixing solution layer 31, a, gel layer 41, a second fixing solution layer 51 and an upper fabric layer 81 of the embodiments are represented by separated and parallel lines respectively in figures. In fact, the above components 20, 31, 41, 51, 81 are connected to each other closely due to crosslinking reaction therebetween or attached to each other closely due to spray coating, dip coating, etc. There is no gap (as shown in figure) between two adjacent components mentioned above.

Figure 1:
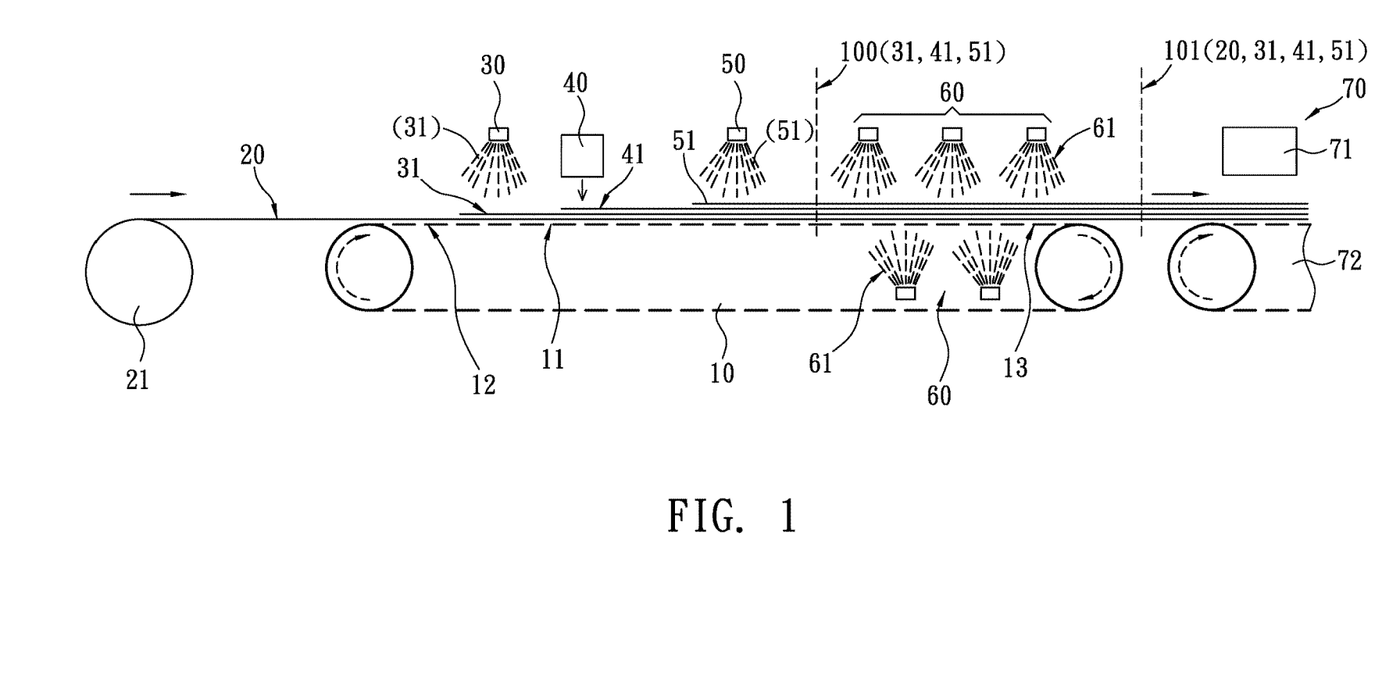
FIG. 1 is an embodiment of an apparatus for continuously manufacturing moisture films without carriers according to the present invention.

Refer to FIG. 1, an apparatus for continuously manufacturing moisture film of the present invention mainly includes at least one belt conveyor 10 with a least one loading surface 11, a lower fabric layer 20 with water absorbency, a first fixing solution coating device 30, a gel coating device 40, and a second fixing solution coating device 50. The three coating devices 30, 40, 50 are arranged over or in front of the loading surface 11 in turn from an input end 12 to an output end 13 along conveying direction of the loading surface 11. The belt conveyor 10 has various forms and the loading surface 11 has different structure according to the form of the belt conveyor 10. The loading surface 11 can be either a continuous surface such as PVC belt conveyor, PU belt conveyor, Teflon belt conveyor, leather belt conveyor, etc., or non-continuous surface such as rolling conveyor, chain conveyor, etc., which is represented by thick broken lines. At least one belt conveyor 10 with a least one loading surface 11 means different combinations of the belt conveyor 10 with the loading surface 11 and there is no limit on the transport way of the belt conveyor 10. The apparatus may include a plurality of belt conveyors 10 each of which has a corresponding loading surface 11. Or a plurality of belt conveyors 10 is connected to form a single loading surface 11. Or a surface of a single belt conveyor 10 is separated into a plurality of segments each of which forms a loading surface 11.

The belt conveyor 10 with at least one loading surface 11 is used as a platform for film-forming, a working surface for continuous formation of moisture films. The circulating loading surface 11 is a flat surface that faces upward and moves along the conveying direction from the input end 12 to the output end 13 circularly. The belt conveyor 10 is designed to have a certain length and a certain width. The loading surface 11 also has a certain length and a certain width so as to form the working surface for forming the moisture film. Moreover, a lower fabric layer 20 with water absorbency is moveably arranged at the loading surface 11 (as shown from FIG. 1 to FIG. 4) or fixed on the loading surface 11 (as shown in FIG. 5). Thus the lower fabric layer 20 is moved synchronously with the loading surface 11. During the synchronous movement, the lower fabric layer 20 is loaded with various film-forming materials such as fixing solutions 31, 51 (sodium compound) and gel 41 (alginate), as shown in FIG. 1. Then a film with a certain thickness is gradually and continuously formed on a top surface of the lower fabric layer 20. That means the film-forming is carried out on the lower fabric layer 20.

As shown in FIG. 1, the lower fabric layer 20 is designed into, but not limited to, a continuous long strip of fabric. A supply source 21 is a roll of lower fabric layer 20. The lower fabric layer 20 is provided continuously by the supply source 21 and passed through the input end 12 to be attached to the circulating loading surface 11 smoothly. In FIG. 1, the lower fabric layer 20 and the loading surface 11 are represented by two separate lines. Then the lower fabric layer 20 is moved synchronously with the loading surface 11 and passed through the output end 12 to be output toward the rear side and left the loading surface 11. After being output, the continuous lower fabric layer 20 is delivered into other predetermined follow-up working equipment 70 for following processes such as automatic or laborious film cutting device 71. For example, another belt conveyor 72 is also used together with the film cutting device 71. Thereby a cutting station is formed and is used for cutting continuous moisture film together with the continuous lower fabric layer 20 into a plurality piece of films. Then the films are treated by other working stations such as trimming working station or packaging working station. The follow-up working equipment 70 includes different working stations or other devices according to various requirements for follow-up operations.

The first fixing solution coating device 30 is used to coat a first fixing solution layer 31 over the lower fabric layer 20 moved together with the loading surface 11. In an embodiment of the present invention, the first fixing solution coating device 30 is arranged over the loading surface 11. As shown in another embodiment of FIG. 4, the first fixing solution coating device 30 can also be disposed in front of the loading surface 11. According to the shape or structure of general moisture film, the first fixing solution layer 31 is evenly spread over the lower fabric layer 20, but not limited. For example, when the moisture film has special structure or shape such as a half-face mask that only covers an upper half or a lower half of user's face, the present invention performs the coating process in an uneven manner. For example, only specific area on the lower fabric layer 20 is coated. Moreover, the way of coating of the present invention is not limited as long as the first fixing solution layer 31 can be formed on the lower fabric layer 20. The way of coating can be spray coating, dip coating or their combination. In FIG. 1, the first fixing solution coating device 30 is coated by spray coating.

As shown in FIG. 1, the gel coating device 40 is arranged at the rear side of the first fixing solution coating device 30. After the first fixing solution layer 31 being coated over the lower fabric layer 20 and moved along with the loading surface 11 to a working range of the gel coating device 40, a gel layer 41 with a certain thickness is coated over the first fixing solution layer 31 by the gel coating device 40. Then the gel layer 41, the first fixing solution layer 31, and the lower fabric layer 20 together with the loading surface 11 are continuously moved backward. During the movement, the first fixing solution layer 31 and the gel layer 41 are crosslinked and gradually cured to form a film.

In this embodiment, the first fixing solution layer 31 is coated over the lower fabric layer 20 first and then the gel layer 41 is coated over the first fixing solution layer 31. Thus the first fixing solution layer 31 is in contact with the lower fabric layer 20 first and may be infiltrate inside through a top surface (or top and bottom surfaces) of the lower fabric layer 20. Yet once a top surface of the first fixing solution layer 31 (containing divalent metal ions) is in contact with the gel layer 41, crosslinking and curing reactions starts immediately. Thus a thin layer of film is formed therebetween. The thin layer of film works like a shielding surface to prevent the gel layer 41 from filtrating inside through the top surface (or bottom surfaces) of the lower fabric layer 20. That means the first fixing solution layer 31 on the surface of the lower fabric layer 20 reacts with the gel layer 41 (from bottom to top) to have crosslinking reaction therebetween and stop infiltrating into the lower fabric layer 20 through the top surface of the lower fabric layer 20 (from top to bottom). Thus a moisture film that is made from hydrogel complex with network structure is formed on the top surface of the lower fabric layer 20. The moisture film (31, 41) formed is easy to be separated from the lower fabric layer 20 while in use. Thus the moisture film of the present invention is considered to have no carrier.

Refer to FIG. 1, the second fixing solution coating device 50 is installed at the rear side of the gel coating device 40. After the gel layer 41 being coated over the first fixing solution layer 31 and moved backward together with the lower fabric layer 20 along the loading surface 11 to a working range of the second fixing solution coating device 50, a second fixing solution layer 51 is coated over the gel layer 41 by the second fixing solution coating device 50. The second fixing solution layer 51, the gel layer 41, the first fixing solution layer 31 and the lower fabric layer 20 are adhered to one another (integrated into one part) and moved backward with the loading surface synchronously after the second fixing solution layer 51 being coated over the gel layer 41. During the movement, the coated second fixing solution layer 51 reacts with the gel layer 41 to initiate crosslinking in the downward direction and gradually curing to form the film. By the crosslinking of the first fixing solution layer 31 with the gel layer 41 and the crosslinking of the second fixing solution layer 51 with the gel layer 41, a film 100 (31, 41, 51) with a certain thickness is formed on the lower fabric layer 20 moved together with the loading surface 11 synchronously to be conveyed backward. Thus the curing period of the film 100 formed over the gel layer 41 is reduced. In other words, the cured film 100 (31, 41, 51) is formed by crosslinking of the first and the second fixing solution layers 31, 51 with the gel layer 41. Thus the cured film 100 in the figure is represented by 31, 41, and 51. Moreover, the film 100 (31, 41, 51) is produced continuously over the lower fabric layer 20 moved backward together with the loading surface 11 synchronously. Thus the film 100 (31, 41, 51) is adhered closely to the lower fabric layer 20 to form a long, continuous strip 101 (20, 31, 41, 51) and moved synchronously with the loading surface 11 to be output through the output end 12 of the loading surface 11. After leaving the loading surface 11, the long, continuous strip 101 (20, 31, 41, 51) is processed by follow-up operations. While leaving the loading surface 11, the film 100 (31, 41, 51) is attached to the lower fabric layer 20 closely to form a long, continuous strip 101 (20, 31, 41, 51). Thus the long, continuous strip 101 in the figure is indicated by the numbers 20, 31, 41, 51. While in use, the film 100 (31, 41, 51) is easily separated from the lower fabric layer 20. Thus a continuous manufacturing of the moisture films without carriers has been completed. The moisture film 100 (31, 41, 51) without carriers is produced rapidly and continuously. Therefore mass production and cost reduction are achieved.

Moreover, the main materials for the first fixing solution layer 31 or the second fixing solution layer 51 include fixing solution required for formation of the film such as salt compound. In practice, the materials for the first fixing solution layer 31 or the second fixing solution layer 51 can also contain other specific ingredient such as essence or serum required for specific functions of the mask such as whitening, anti-wrinkle treatment etc.

Figure 2:
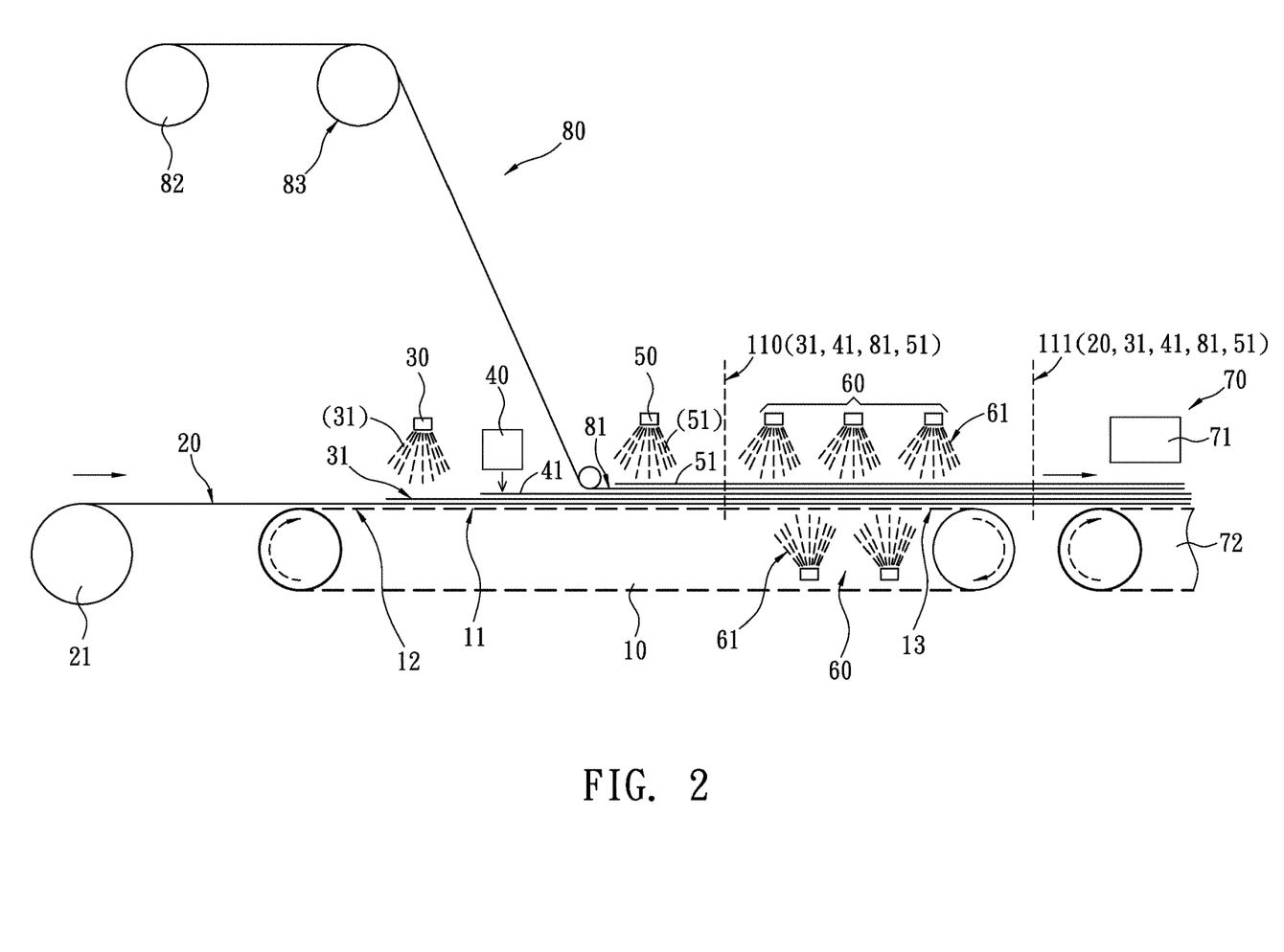
FIG. 2 is another embodiment of an apparatus for continuously manufacturing moisture films with carriers according to the present invention.

Refer to FIG. 2, another embodiment is revealed. The difference between this embodiment and the above one is in that an upper fabric input device 80 for providing an upper fabric layer 81 is disposed between the gel coating device 40 and the second fixing solution coating device 50. In the figure, the upper fabric layer 81 is flat against the gel layer 41 first. The second fixing solution layer 51 is coated over the upper fabric layer 81 at the same time or later. The upper fabric layer 81 is first in contact with the gel layer 41 so that the gel layer 41 is infiltrated into an inner layer of the upper fabric layer 81 through a bottom surface of the upper fabric layer 81. Thus when the second fixing solution layer 51 is coated over the upper fabric layer 81 that has been infiltrated by the gel layer 41, the second fixing solution layer 51 can be infiltrate into the inner layer of the upper fabric layer 81 through a top surface of the upper fabric layer 81 to react with the gel layer 41 already infiltrated into the inner layer of the upper fabric layer 81 and form crosslinking therebetween. By crosslinking between the first fixing solution layer 31 and the gel layer 41 in the upward direction and crosslinking between the second fixing solution layer 51 and the gel layer 41 in the downward direction, the upper fabric layer 81 is clipped or contained between the second fixing solution layer 51 and the gel layer 41. Thereby during the backward movement of the lower fabric layer 20 with the loading surface 11, a film 110 (31, 41, 81, 51) with a certain thickness and having the upper fabric layer 81 is gradually formed on the top surface of the lower fabric layer 20, as shown in FIG. 2. Thus a continuous manufacturing of the moisture film with carriers has been completed.

In the second embodiment, the upper fabric layer 81 provided by the upper fabric input device 80 is, but not limited to, a long, continuous strip of fabric. The long, continuous strip of the upper fabric layer 81 in FIG. 2 is wound into a roll, used as a supply source 82 for continuous supply of the upper fabric layer 81 and smooth attachment of the upper fabric layer 81 to the gel layer 41. Moreover, the use of mechanical elements such as idle gear 83 or their combinations such as idle gear set can improve convenience in operation or precision of operation of the upper fabric input device 80. Thus the upper fabric layer 81 can be flat attached to the gel layer 41 easily and precisely.

Figure 3:
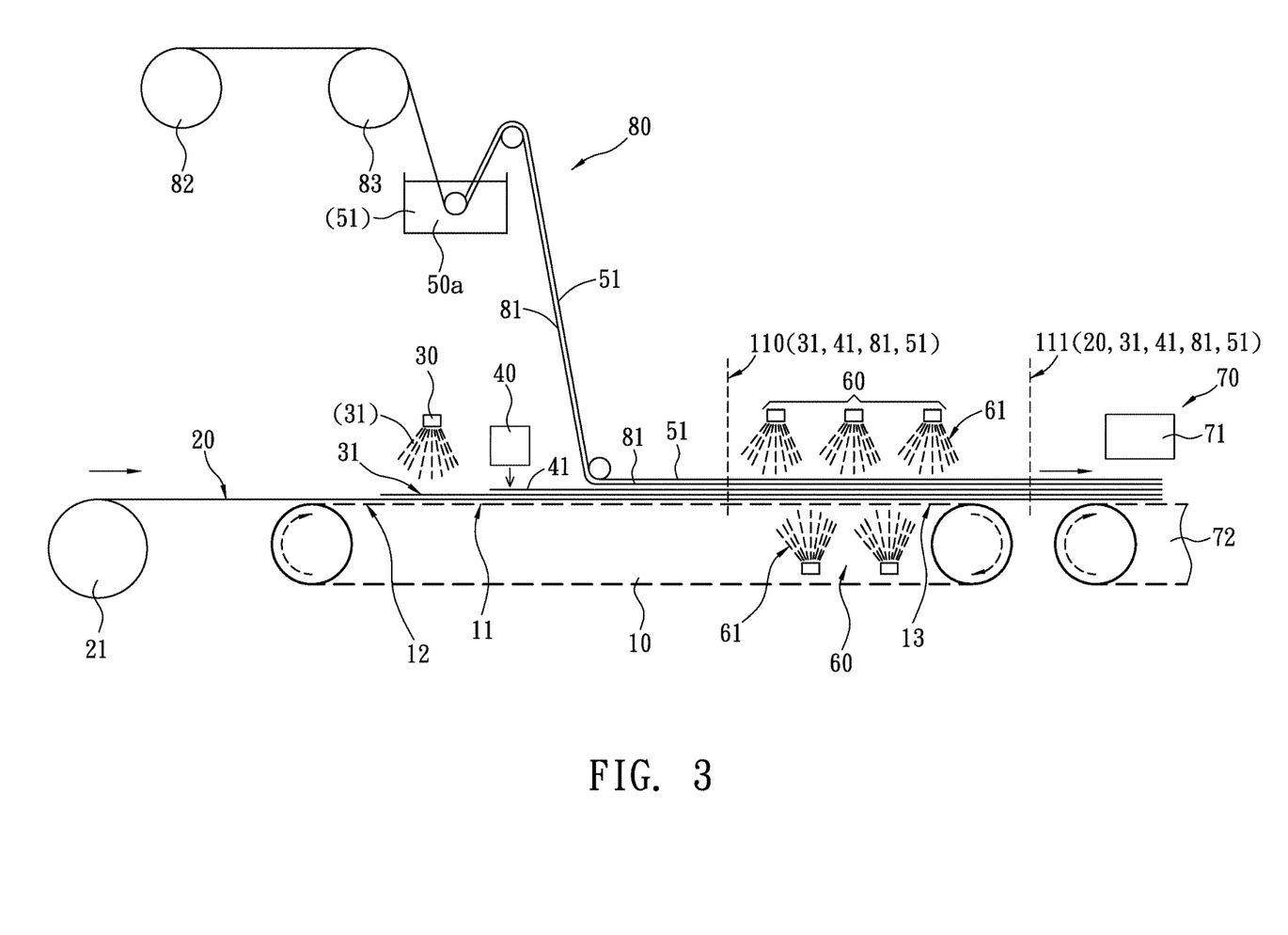
FIG. 3 is a third embodiment of an apparatus for continuously manufacturing moisture films without carriers according to the present invention.

Furthermore, there is no limit on the order of the time point of the second fixing solution layer 51 being coated over the upper fabric layer 81 and the time point of the upper fabric layer 81 being flat attached to the gel layer 41 correspondingly. As shown in FIG. 2, the upper fabric layer 81 is flat attached to the gel layer 41 correspondingly and then the second fixing solution layer 51 is coated over the upper fabric layer 81 by spray coating in the downward direction. Or both of the procedures are carried out at the same time. Thus a continuous manufacturing of the moisture film with carriers has been completed. Refer to FIG. 3, the second fixing solution layer 51 is coated over the upper fabric layer 81 by dip coating. Then the upper fabric layer 81 coated with the second fixing solution layer 51 is attached to the gel layer 41 smoothly and correspondingly. Due to the second fixing solution layer 51 existed between the upper fabric layer 81 and the gel layer 41, the upper fabric layer 81 in FIG. 3 can be easily separated from the film 110 (31, 41, 81, 51) formed. Thus a continuous manufacturing of the moisture film without carriers as shown in FIG. 3 is revealed.

In FIG. 2, the film 110 is formed by crosslinking between the first fixing solution layer 31 and the gel layer 41 in the upward direction as well as crosslinking between the second fixing solution layer 51 and the gel layer 41 in the downward direction and through the upper fabric layer 81. Thus the upper fabric layer 81 in the film 110 (31, 41, 81, 51) formed is unable to be separated from the film 110 (31, 41, 81, 51) easily. Compared the second embodiment in FIG. 2 with the first embodiment in FIG. 1, the film 110 (31, 41, 81, 51) of the second embodiment including the upper fabric layer 81 integrated therewith is formed continuously on the lower fabric layer 20 that is moved backward with the loading surface 11 synchronously. In practice, the film 110 (31, 41, 81, 51) and the lower fabric layer 20 are adhered to form a long, continuous strip 111 (20, 31, 41, 81, 51). As shown in FIG. 2, the long, continuous strip 111 (20, 31, 41, 81, 51) is moved synchronously with the loading surface 11 to be output through the output end 12 of the loading surface 11. After leaving the loading surface 11, the long, continuous strip 111 (20, 31, 41, 81, 51) is processed by follow-up operations. During follow-up operations, the film 110 (31, 41, 81, 51) and the lower fabric layer 20 are still adhered to each other to form the long, continuous strip 111 (20, 31, 41, 81, 51). While in use, the film 110 (31, 41, 81, 51) can be easily separated from the lower fabric layer 20 after being cut into various shapes of masks ready to use. Yet the film 110 (31, 41, 81, 51) of the second embodiment includes the upper fabric layer 81. Thus the film 110 (31, 41, 81, 51) of the second embodiment is considered as the moisture film with carriers in the present invention. Therefore the second embodiment reveals a continuous manufacturing of the moisture film with carriers. The moisture film 110 (31, 41, 81, 51) with carriers is produced rapidly and continuously so as to achieve mass production and cost reduction.

Moreover, a continuous manufacturing of moisture films without carriers shown in FIG. 1 (the first embodiment) is converted into a continuous manufacturing of moisture films with carriers shown in FIG. 2 (the second embodiment) by the arrangement of the upper fabric input device 80 and disposition of the upper fabric layer 81 provided by the upper fabric input device 80. Thus manufacturers can determine to produce the moisture films with carriers or without carriers easily and conveniently according to consumers' requirements. Thus not only mass production and cost reduction are achieved, consumers also have more options of moisture films and convenience of use.

Refer to FIG. 1 and FIG. 2, a crosslinking control area 60 is disposed on the rear side of the second fixing solution coating device 50. The crosslinking control area 60 includes, but not limited to, at least one crosslinking control device. From FIG. 1 to FIG. 5, the crosslinking control area 60 includes three and two spray-type crosslinking control devices respectively arranged at the top surface and the bottom surface of the loading surface 11 (or the lower fabric layer 20), but not limited to. The crosslinking control area 60 is used for washing the film 100 (31, 41, 51) formed in FIG. 1 or the film 110 (31, 41, 81, 51) shown in FIG. 2. The crosslinking reaction between the fixing solution layers 31, 51 and the gel layer 41 is stopped by the washing process provided in the crosslinking control area 60. For example, a part of the fixing solution 31, 51 not reacted yet is washed out by pure water. Or the crosslinking reaction between the fixing solution layers 31, 51 and the gel layer 41 is stopped directly by crosslinking stop solution. Thus the crosslinking and curing reactions between the first and second fixing solution layers 31, 51 and the gel layer 41 can be controlled or stopped. By controlling washing period or travel distance of the crosslinking control area 60, a part of the fixing solutions in the fixing solution layers 31, 51 is washed out so as to reduce reaction time and degree of the crosslinking and curing reactions between the first and second fixing solution layers 31, 51 and the gel layer 41 and avoid over-curing. Thereby the film 100 (31, 41, 51) or the film 110 (31, 41, 81, 51) formed is more flexible.

In addition, crosslinking control solution 61 of the crosslinking control area 60 can be either water used for washing, or crosslinking stop solution for stopping the crosslinking reaction between the fixing solution layers 31, 51 and the gel layer 41. In practice, the crosslinking control solution 61 can also be added with specific ingredients such as cosmetic essence/serum according to additional functions such as whitening, anti-wrinkle treatment, etc. the mask requires.

Refer to FIG. 3, a further embodiment is disclosed. The difference between this embodiment and the above one in FIG. 2 is in that the coating way of the second fixing solution coating device 50 in FIG. 2 is changed into a dip coating carried out by a dip-type second fixing solution coating device 50a. Thereby an upper fabric layer 81 provided by an upper fabric input device 80 is first passed through the dip-type second fixing solution coating device 50*a*. As shown in FIG. 3, then a second fixing solution layer 51 represented by a parallel line is coated over the upper fabric layer 81. Yet the second fixing solution layer 51 can be, but not limited to, coated over one surface of the upper fabric layer 81. In this embodiment, the upper fabric layer 81 can be easily removed from the film 110 (31, 41, 81, 51). A continuous manufacturing of moisture films without carriers is shown in FIG. 3.

Figure 4:
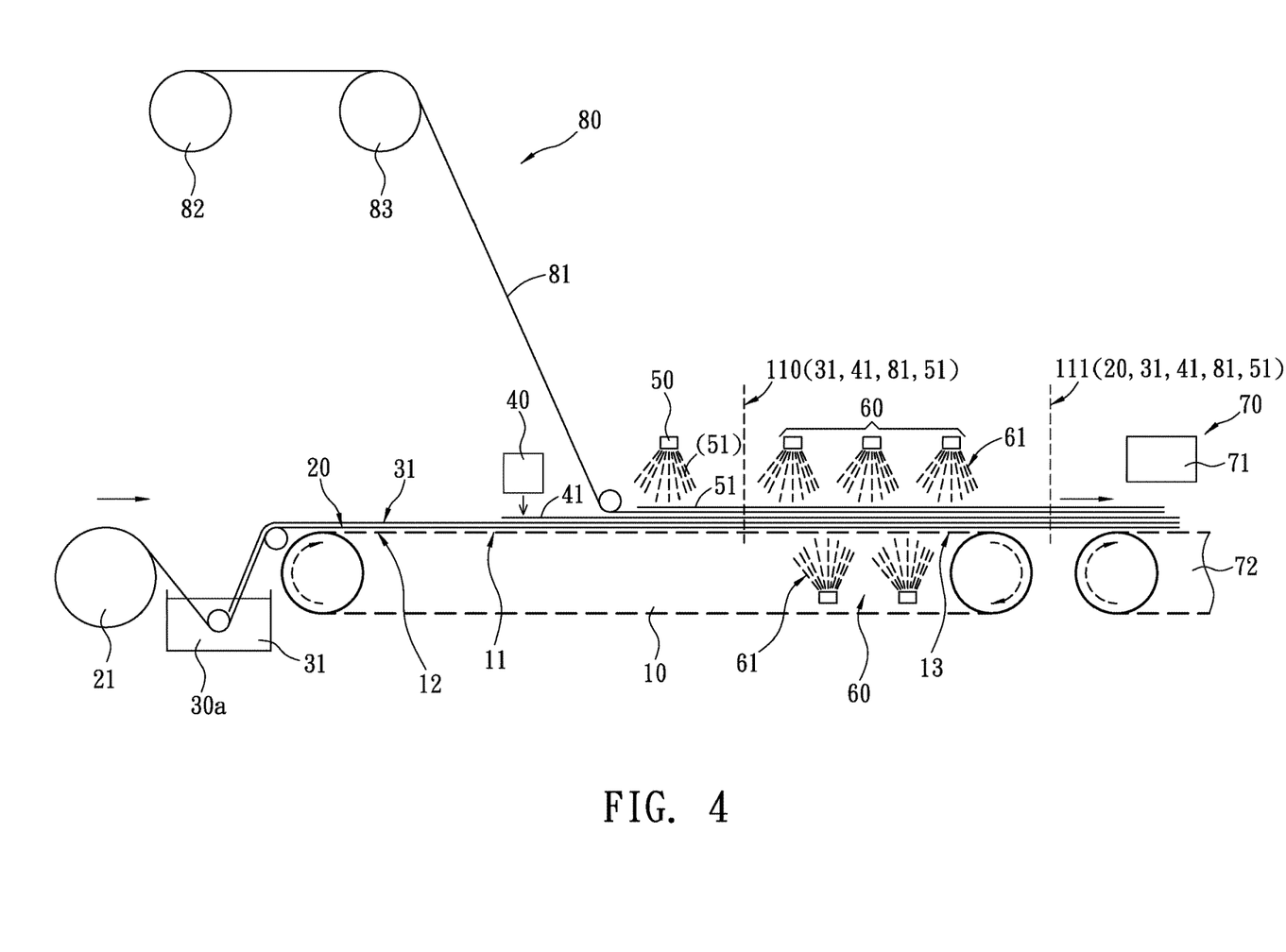
FIG. 4 is a fourth embodiment of an apparatus for continuously manufacturing moisture films with carriers according to the present invention.
Figure 5:
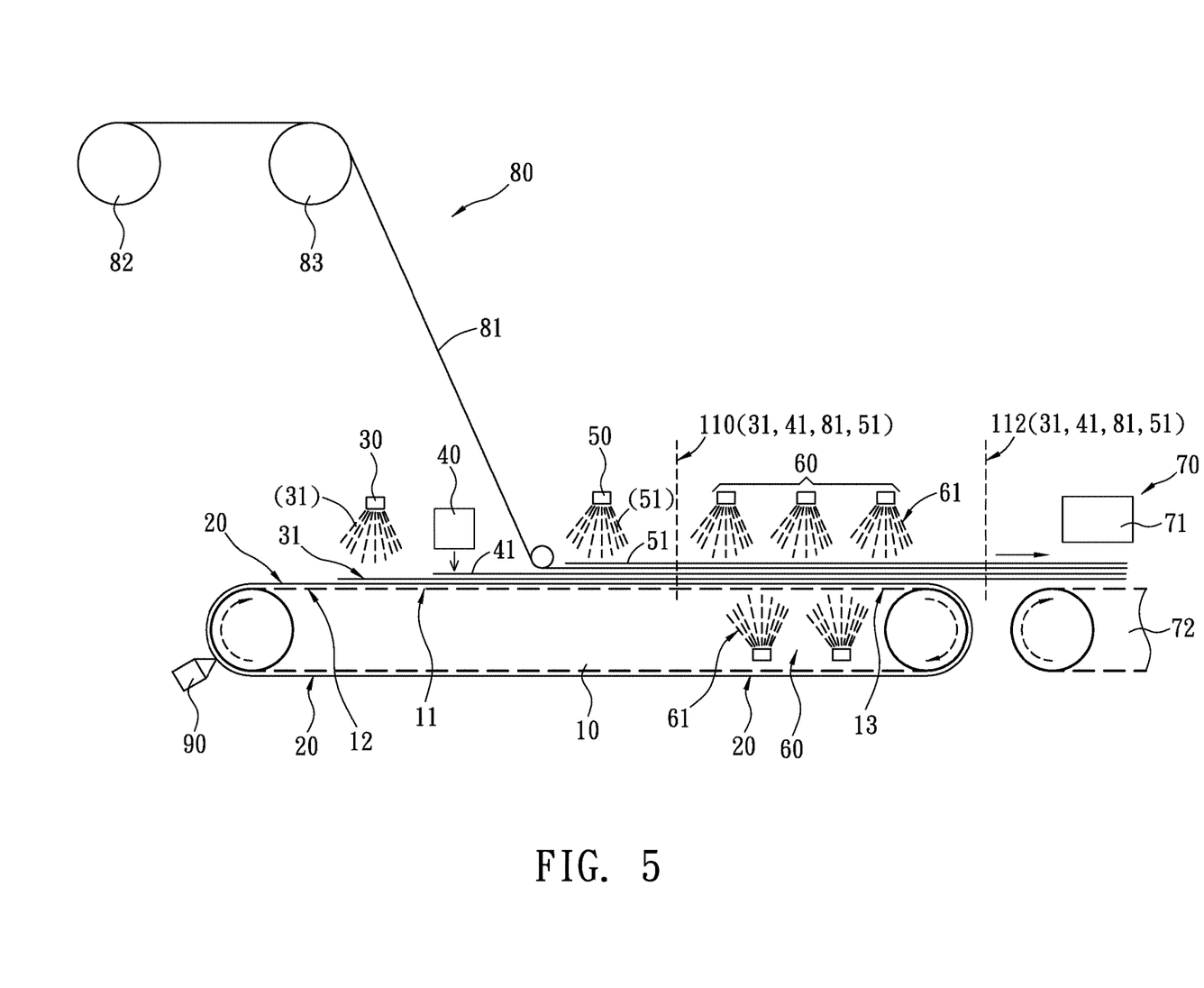
FIG. 5 is a fifth embodiment of an apparatus for continuously manufacturing moisture films with carriers according to the present invention.

Refer to FIG. 4, the difference of the embodiment in the figure and the second embodiment shown in FIG. 2 is in that the first fixing solution coating device 30 of the second embodiment is replaced by an equivalent dip-type first fixing solution coating device 30*a*. Thereby the lower fabric layer 20 provided by a lower fabric input device 21 is first passed through the dip-type first fixing solution coating device 30*a*. As shown in FIG. 4, then a first fixing solution layer 31 represented by a parallel line is coated over the lower fabric layer 20. Yet the first fixing solution layer 31 is not limited to be coated over the top surface of the lower fabric layer 20. Thereby the first fixing solution coating device 30*a* of the embodiment achieves the same use and function as the first fixing solution coating device 30 in the second embodiment shown in FIG. 2 (or the first embodiment in FIG. 1). That means the first fixing solution layer 31 is coated over the lower fabric layer 20 which is moved backward synchronously with the loading surface 11 by the first fixing solution coating device 30*a*.

Refer to FIG. 5, a further embodiment is revealed. The difference between the fifth embodiment and the above four embodiments is in that the lower fabric layer 20 of this embodiment with water absorbency is fixed on and moved backward synchronously with the loading surface 11 while the lower fabric layer 20 with water absorbency of the above embodiments is moveably arranged at and moved backward synchronously with the loading surface 11. Due to that the lower fabric layer 20 is fixed on the surface of the belt conveyor 10, the lower fabric layer 20 is moved and rotated synchronously with the belt conveyor 10. Thus the lower fabric layer 20 forms the circulating loading surface 11 shown in FIG. 1 to FIG. 4 that is used as a working surface for continuous formation of the moisture film when the lower fabric layer 20 is rotated to the top surface of the belt conveyor 10 along with the belt conveyor 10. The use and function of the lower fabric layer 20 can still be achieved. In practice, the film 110 (31, 41, 81, 51) in the fifth embodiment is attached to the lower fabric layer 20 to be moved backward synchronously as long as the film 110 (31, 41, 81, 51) still stays on and moved backward synchronously with the loading surface 11, no matter the film (31, 41, 81, 51) is having crosslinking and curing reactions, already formed or being washed by the crosslinking control area 60. When the film 110 (31, 41, 81, 51) is output through the output end 12 of the loading surface 11, the film 110 (31, 41, 81, 51) is separated from the lower fabric layer 20 to form a long, continuous strip 112 (31, 41, 81, 51) for follow-up operations, as shown in FIG. 5. The long, continuous strip 112 (31, 41, 81, 51) output through the output end 12 of the loading surface 11 in the fifth embodiment is different from the long, continuous strip 111 (20, 31, 41, 81, 51) in the embodiments 2, 3 and 4 because that the lower fabric layer 20 of the fifth embodiment is fixed on the loading surface 11, not being moved backward with the long, continuous strip 112 (31, 41, 81, 51) to be processed by follow-up operations.

In the fifth embodiment, the lower fabric layer 20 fixed on the surface of the belt conveyor 10 is rotated circularly and synchronously with the belt conveyor 10 and all coating processes are carried out under an open state. Thus there may be a part of film-forming material such as fixing solutions, 21, 51, gel 41 or film 110 already formed residual on the circulating loading surface 11 and/or the lower fabric layer 20. This may result in damages on the film 110 (31, 41, 81, 51) formed in the next cycle. Thus a scraping and cleaning tool 90 such as a scraper is arranged at the apparatus. When the lower fabric layer 20 or the circulating loading surface 11 continues to rotate and form the loading surface 11 of the next cycle, the residues on the circulating loading surface 11 or the lower fabric layer 20 are removed or cleaned up by the scraping and cleaning tool 90 so as to prevent the quality of the film 110 (31, 41, 81, 51) from being affected by the residues.

Moreover, the fourth and the fifth embodiments of the present invention are modified by and equivalent to the second embodiment that is an apparatus/or method for continuous manufacturing of a moisture film with carriers. But these two embodiments are not limited to be equivalent to the second embodiment. They can also be equivalent to the first embodiment that is an apparatus/or method for continuous manufacturing of a moisture film without carriers.

Figure 6:
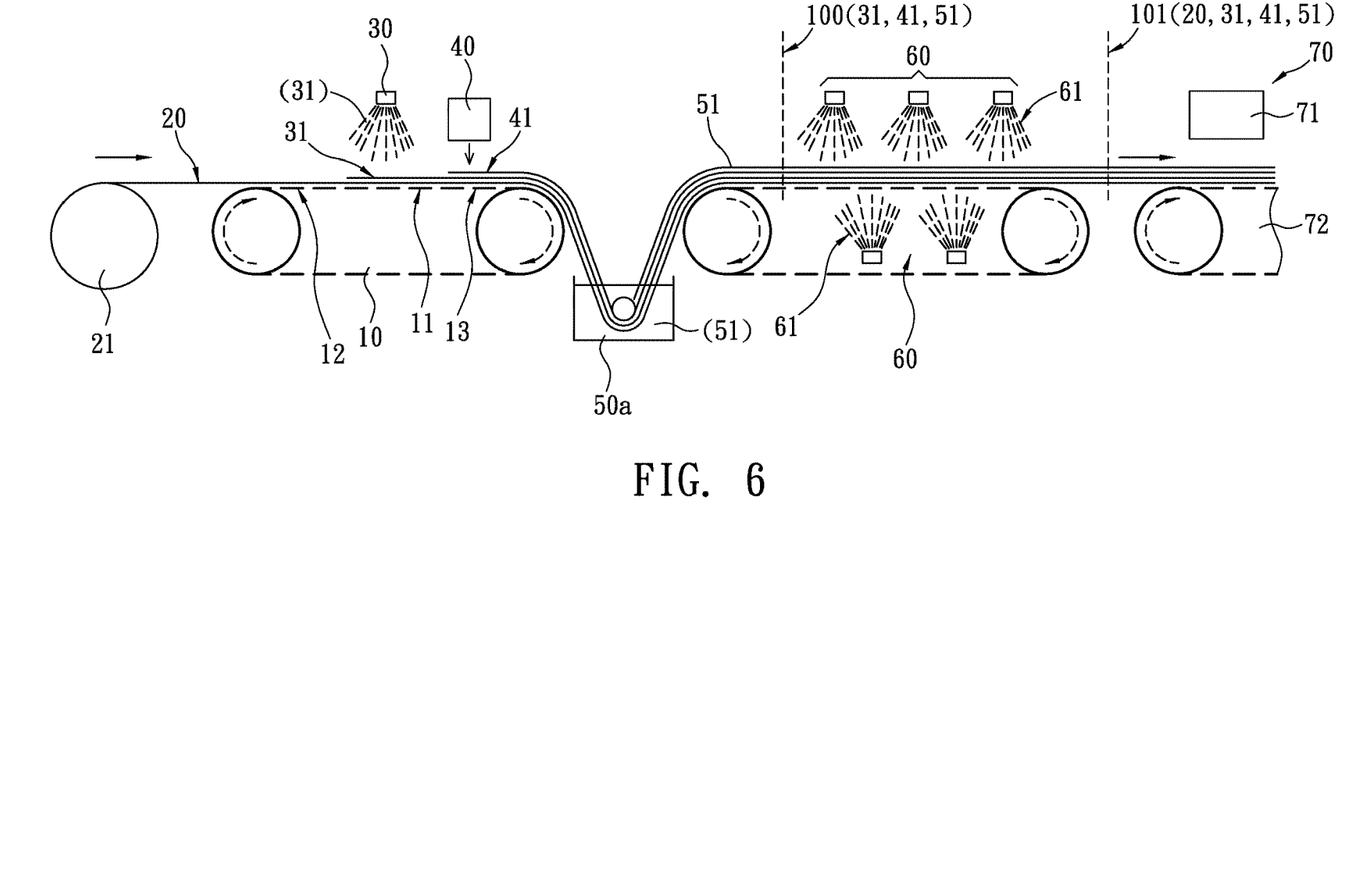
FIG. 6 is a sixth embodiment of an apparatus for continuously manufacturing moisture films without carriers according to the present invention.

Refer to FIG. 6, a further embodiment is disclosed. The difference between this (the sixth) embodiment and the first embodiment shown in FIG. 1 is in that the spray-type second fixing solution coating device 50 of the first embodiment is replaced by an equivalent dip-type second fixing solution coating device 50*a*. Thereby the assembly 20, 31, 41 of the first fixing solution layer 31, the gel layer 41 and the lower fabric layer 20 formed after the gel layer 41 being coated over the first fixing solution layer 31 is continuously moved backward to pass through the dip-type second fixing solution coating device 50*a*. Then the gel layer 41 is added with a second fixing solution layer 51 represented by a parallel line, but the second fixing solution layer 51 is not limited to be only dip-coated over the top surface of the gel layer 41. The second fixing solution coating device 50*a* of this embodiment provides the same use and function as the second fixing solution coating device 50 of the first embodiment in FIG. 1. That means a second fixing solution layer 51 is coated over the assembly 20, 31, 41 moved backward by the dip-type second fixing solution coating device 50*a*.

Furthermore, in the sixth embodiment, the loading surface 11 can be considered as a two-stage loading surface 11, disposed in front of and at the rear end of the dip-type second fixing solution coating device 50*a* respecctively. Or the loading surface 11 is considered as two separated loading surfaces 11 each of which is formed by a belt conveyor 10.

Figure 7:
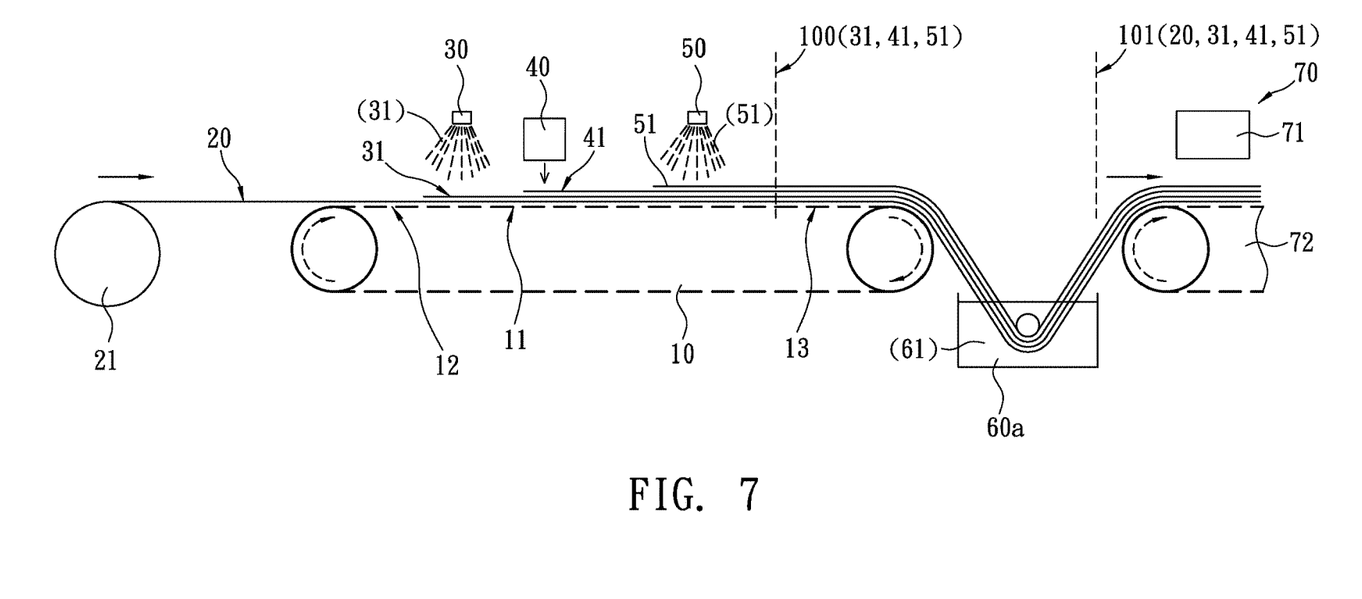
FIG. 7 is a seventh embodiment of an apparatus for continuously manufacturing moisture films without carriers according to the present invention.

As shown in FIG. 7, a seventh embodiment is disclosed. The difference between this (the seventh) embodiment and the first embodiment shown in FIG. 1 is in that the spray-type crosslinking control area 60 of the first embodiment is replaced by an equivalent dip-type crosslinking control area 60*a*. When the film 100 (31, 41, 51) and the lower fabric layer 20 have been connected to form an assembly (20, 31, 41, 51) and the assembly (20, 31, 41, 51) has been moved backward with the loading surface 11 synchronously to be output and passed through the dip-type crosslinking control area 60*a*, crosslinking control solution 61 of the crosslinking control area 60 is used to wash the fixing solution layer residual in the film 100 (31, 41, 51) and/or the gel layer 41, or directly stopping the crosslinking reaction between the fixing solution layers 31, 51 and the gel layer 41. Thus the dip-type crosslinking control area 60a has the same use and function as the spray-type crosslinking control area 60 of the first embodiment.

Figure 8:
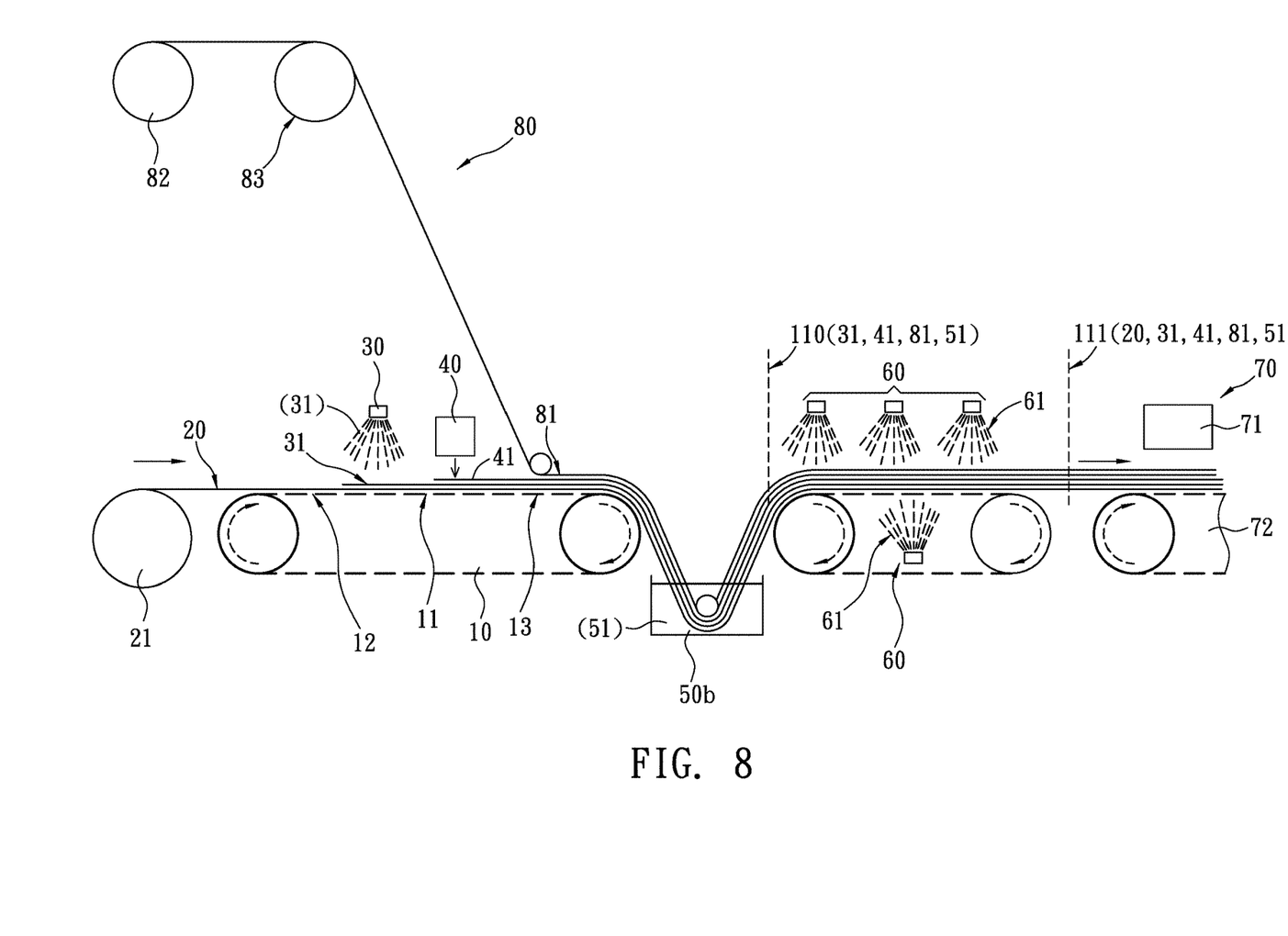
FIG. 8 is an eighth embodiment of an apparatus for continuously manufacturing moisture films with carriers according to the present invention.

Refer to FIG. 8, a further embodiment is revealed. The difference between this (the eighth) embodiment and the second embodiment shown in FIG. 2 is in that the spray-type second fixing solution coating device 50 of the second embodiment is replaced by an equivalent dip-type second fixing solution coating device 50b. After the gel layer 41 has been coated over the first fixing solution layer 31 and the upper fabric layer 81 has been attached to the gel layer 41 smoothly, the assembly 20, 31, 41, 81 formed by the first fixing solution layer 31, the gel layer 41, the upper fabric layer 81 and the lower fabric layer 20 is moved backed with the loading surface 11 synchronously and continuously to pass through the dip-type second fixing solution coating device 50b. Then as shown in FIG. 8, a second fixing solution layer 51 represented by a parallel line is added over the gel layer 41. Yet the second fixing solution layer 51 is not limited to be added only over the top surface of the gel layer 41. Thereby the dip-type second fixing solution coating device 50b of this embodiment has the same use and function as the second fixing solution coating device 50 of the second embodiment shown in FIG. 2 (or the second fixing solution coating device 50a of the sixth embodiment). That means a second fixing solution layer 51 is coated over the assembly (20, 31, 41, 81) moved backward by the dip-type second fixing solution coating device 50b. Moreover, the structure of the loading surface 11 in this embodiment is similar to the two-stage loading surface 11 or two separated loading surfaces 11 of the sixth embodiment.

Figure 9:
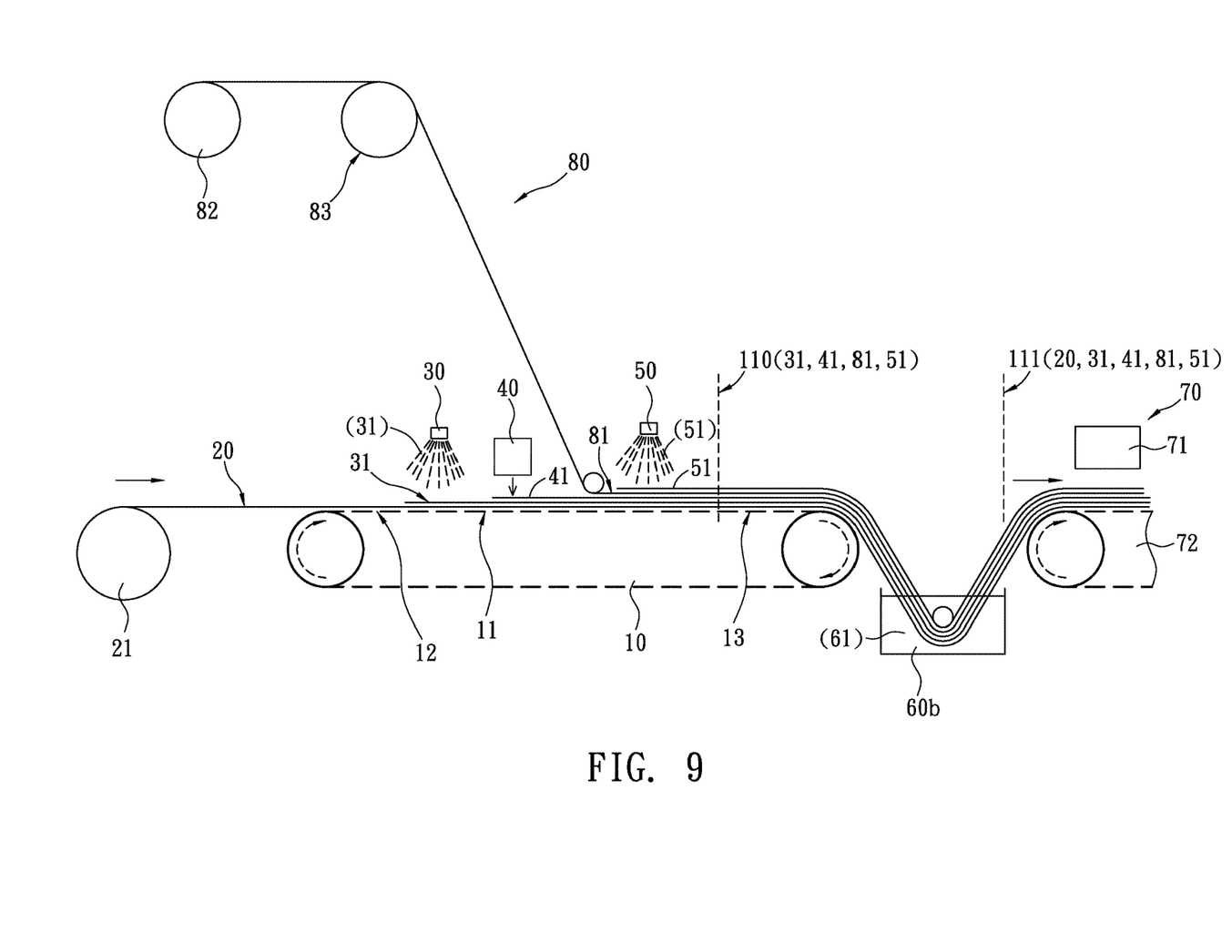
FIG. 9 is a ninth embodiment of an apparatus for continuously manufacturing moisture films with carriers according to the present invention.

Refer to FIG. 9, a ninth embodiment is disclosed. The difference between this embodiment and the second embodiment shown is in that the spray-type crosslinking control area 60 of the second embodiment is replaced by an equivalent dip-type crosslinking control area 60b. When the film 110 (31, 41, 81, 51) and the lower fabric layer 20 has been moved backward with the loading surface 11 synchronously to be output, the film 110 (31, 41, 81, 51) is continuously delivered backward to pass through the dip-type crosslinking control area 60b. In the dip-type crosslinking control area 60b shown in FIG. 9, crosslinking control solution 61 is used to wash the fixing solution layers 31, 51 residual in the film 110 (31, 41, 81, 51), or the gel layer 41, or directly stopping the crosslinking reaction between the fixing solution layers 31, 51 and the gel layer 41. Thus this embodiment has the same function and purpose as the spray-type crosslinking control area 60 of second embodiment or the dip-type crosslinking control area 60a of the seventh embodiment.

By means of the apparatus for continuously manufacturing moisture films mentioned above, the present invention provides a method for continuously manufacturing moisture films without carriers that includes following steps:

Step 1: provide at least one circulating loading surface used as a working platform for film-forming. The loading surface is a flat surface facing upward and moved circularly along a conveying direction from an input end to an output end.

Step 2: provide a lower fabric layer with water absorbency that is moved synchronously with the loading surface for receiving various film-forming materials in turn and performing film-forming operation.

Step 3: provide a first fixing solution coating device that coats a first fixing solution layer over the lower fabric layer by spray coating or dip coating.

Step 4: provide a gel coating device for coating a gel layer over the first fixing solution layer and having crosslinking and curing reactions between the gel layer and the first fixing solution layer.

Step 5: provide a second fixing solution coating device used to coat a second fixing solution layer over the gel layer for carrying out crosslinking and curing reactions between the second fixing solution layer and the gel layer. The second fixing solution layer is coated over the gel layer by spray coating or dip coating. Thus a film with a certain thickness is gradually formed on a top surface of the lower fabric layer moved synchronously with the loading surface. Therefore a continuous manufacturing of the moisture film without carriers is completed.

Moreover, the method further includes a step 6 after the step 5-provide a crosslinking control area that controls crosslinking reaction in the film gradually formed on the lower fabric layer. By at least one crosslinking stop solution that is distributed by spray coating or dip coating in the crosslinking control area, the crosslinking reaction between the first fixing solution layer and the gel layer and/or the crosslinking reaction between the second fixing solution layer and the gel layer is stopped or washed out.

By means of the apparatus for continuously manufacturing moisture films mentioned above, the present invention provides a method for continuously manufacturing moisture films with carriers that includes following steps:

Step 1: provide at least one circulating loading surface used as a working platform for film-forming. The loading surface is a flat surface facing upward and moved circularly along a conveying direction from an input end to an output end.

Step 2: provide a lower fabric layer with water absorbency that is moved synchronously with the loading surface for receiving various film-forming materials in turn and performing film-forming operation.

Step 3: provide a first fixing solution coating device that coats a first fixing solution layer over the lower fabric layer by spray coating or dip coating.

Step 4: provide a gel coating device for coating a gel layer over the first fixing solution layer and having crosslinking and curing reactions between the gel layer and the first fixing solution layer.

Step 5: provide an upper fabric layer attached over the gel layer correspondingly.

Step 6: provide a second fixing solution coating device used to coat a second fixing solution layer over the upper fabric layer by spray coating or dip coating for carrying out crosslinking and curing reactions between the second fixing solution layer and the gel layer; thereby the upper fabric layer is clipped between the second fixing solution layer and the gel layer due to the crosslinking reaction therebetween; a film with a certain thickness and containing the upper fabric layer is gradually formed on a top surface of the lower fabric layer that is moved synchronously with the loading surface and a continuous manufacturing of the moisture film with carriers is completed.

Furthermore, the method includes a step 7 after the above step 6. Provide a crosslinking control area used for control of crosslinking reaction in the film gradually formed on the lower fabric layer. At least one crosslinking control solution of the crosslinking control area is used for washing and stopping the crosslinking reaction between the second fixing solution layer and the gel layer and/or the second fixing solution layer and the gel layer. The crosslinking control solution is sprayed over the film or the film is dipped therein.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method for continuously manufacturing moisture films comprising the steps of:
    Step 1: providing at least one circulating loading surface used as a working platform for film-forming and the loading surface including a flat surface facing upward and moved circularly along a conveying direction from an input end to an output end;
    Step 2: providing a lower fabric layer with water absorbency that is moved synchronously with the loading surface for receiving various film-forming materials in turn;
    Step 3: providing a first fixing solution coating device and coating a first fixing solution layer over the lower fabric layer by spray coating or dip coating;
    Step 4: providing a gel coating device and coating a gel layer over the first fixing solution layer and having crosslinking and curing reactions between the gel layer and the first fixing solution layer;
    Step 5: providing a second fixing solution coating device and coating a second fixing solution layer over the gel layer by spray coating or dip coating for carrying out crosslinking and curing reactions between the second fixing solution layer and the gel layer; thereby gradually forming a moisture film with a certain thickness on a top surface of the lower fabric layer that is moved synchronously with the loading surface and a continuous manufacturing of the moisture films without carriers is completed; and
    Step 6: after Step 5 providing a crosslinking control area and distributing at least one crosslinking stop solution in the crosslinking control area by spray coating or dip coating so as to stop or wash out the crosslinking reaction between the first fixing solution layer and the gel layer and the crosslinking reaction between the second fixing solution layer and the gel layer.

2. A method for continuously manufacturing moisture films comprising the steps of:
    Step 1: providing at least one circulating loading surface used as a working platform for film-forming and the loading surface including a flat surface facing upward and moved circularly along a conveying direction from an input end to an output end;
    Step 2: providing a lower fabric layer with water absorbency that is moved synchronously with the loading surface for receiving various film-forming materials in turn;
    Step 3: providing a first fixing solution coating device and coating a first fixing solution layer over the lower fabric layer by spray coating or dip coating;
    Step 4: providing a gel coating device and coating a gel layer over the first fixing solution layer and having crosslinking and curing reactions between the gel layer and the first fixing solution layer; and
    Step 5: providing an upper fabric layer attached over the gel layer correspondingly;
    Step 6: providing a second fixing solution coating device and coating a second fixing solution layer over the upper fabric layer by spray coating or dip coating for carrying out crosslinking and curing reactions between the second fixing solution layer and the gel layer; thereby the upper fabric layer is clipped between the second fixing solution layer and the gel layer due to the corsslinking reaction therebetween; gradually forming a moisture film with a certain thickness and containing the upper fabric layer on a top surface of the lower fabric layer that is moved synchronously with the loading surface and a continuous manufacturing of the moisture films with carriers is completed.

3. The method as claimed in claim 2, wherein after the step 6, the method further includes a step 7 of providing a crosslinking control area and distributing at least one crosslinking stop solution in the crosslinking area by spray coating or dip coating so as to stop or wash out the crosslinking reaction between the first fixing solution layer or the gel layer and the crosslinking reaction between the second fixing solution layer and the gel layer.

* * * * *